United States Patent
Parchak et al.

(10) Patent No.: US 10,359,464 B2
(45) Date of Patent: Jul. 23, 2019

(54) CABLE AND ASSOCIATED CONTINUITY MONITORING SYSTEM AND METHOD

(71) Applicant: Biosense Webster (Israel) Ltd., Yokneam (IL)

(72) Inventors: Yochai Parchak, Raanana (IL); Eyal Rotman, Kiriat Tivon (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 23 days.

(21) Appl. No.: 15/707,558

(22) Filed: Sep. 18, 2017

(65) Prior Publication Data

US 2019/0086465 A1   Mar. 21, 2019

(51) Int. Cl.
  *G01R 31/02* (2006.01)
  *A61B 18/14* (2006.01)
  *A61B 5/042* (2006.01)

(52) U.S. Cl.
  CPC ............ *G01R 31/026* (2013.01); *A61B 5/042* (2013.01); *A61B 18/1492* (2013.01); *G01R 31/021* (2013.01); *A61B 2560/0276* (2013.01); *A61B 2562/222* (2013.01)

(58) Field of Classification Search
  CPC ........ G01R 31/026; G01R 31/021–023; A61B 5/042–0422; A61B 18/1492; A61B 2562/222; A61B 2560/0276
  USPC ................................................. 324/539–544
  See application file for complete search history.

(56) References Cited

U.S. PATENT DOCUMENTS

| | | | | |
|---|---|---|---|---|
| 2,731,598 A | * | 1/1956 | Herbert | G01R 31/08 200/61.62 |
| 2,852,737 A | * | 9/1958 | Wheeler | G01R 31/041 324/512 |
| 3,113,266 A | * | 12/1963 | Lehman | G01R 31/08 324/527 |
| 4,389,694 A | * | 6/1983 | Cornwell, Jr. | H02H 5/10 324/527 |
| 5,391,199 A | | 2/1995 | Ben-Haim | |
| 5,443,489 A | | 8/1995 | Ben-Haim | |
| 5,558,091 A | | 9/1996 | Acker et al. | |
| 5,944,022 A | | 8/1999 | Nardella et al. | |
| 5,983,126 A | | 11/1999 | Wittkampf | |
| 6,172,499 B1 | | 1/2001 | Ashe | |
| 6,177,792 B1 | | 1/2001 | Govari et al. | |
| 6,690,963 B2 | | 2/2004 | Ben-Haim et al. | |

(Continued)

*Primary Examiner* — Patrick Assouad
*Assistant Examiner* — Demetrius R Pretlow
(74) *Attorney, Agent, or Firm* — Volpe and Koenig, P.C.

(57) ABSTRACT

A cable, an associated monitoring system and methods are provided which monitor the continuity of current of electrical components such as sensor signals from sensors used in connection with a medical apparatus. The cable includes a proximal end for coupling with a processing unit and a distal end with or for coupling to sensors. The processing unit generates a continuity signal that travels through the cable via an inductor coil conductor to a distal end inductor coil which imparts the signal to sensor signal conductors of the cable. The continuity signal is carried back to the processing unit with signals from the sensors. Circuitry of the processing unit can detect the returning continuity signals to indicate proper connectivity of the sensor signals. The connection status information of the sensors can be displayed to inform a doctor or other operator of the medical apparatus of sensor signal continuity.

20 Claims, 5 Drawing Sheets

(56) References Cited

U.S. PATENT DOCUMENTS

| | | |
|---|---|---|
| 6,788,967 B2 | 9/2004 | Ben-Haim et al. |
| 8,686,738 B2 * | 4/2014 | Sexton .................... H02H 3/10 |
| | | 324/539 |
| 8,797,714 B2 * | 8/2014 | Balji .................... A61B 5/0002 |
| | | 361/437 |
| 9,314,208 B1 * | 4/2016 | Altmann .............. A61B 5/6858 |
| 2003/0018326 A1 | 1/2003 | Abboud et al. |
| 2005/0182398 A1 * | 8/2005 | Paterson ............ A61B 18/1233 |
| | | 606/34 |
| 2008/0091065 A1 | 4/2008 | Oshima et al. |
| 2008/0306380 A1 * | 12/2008 | Parchak ................. A61B 5/042 |
| | | 600/424 |
| 2009/0093806 A1 | 4/2009 | Govari et al. |
| 2009/0138007 A1 | 5/2009 | Govari et al. |
| 2011/0015533 A1 | 1/2011 | Cox et al. |
| 2011/0210750 A1 * | 9/2011 | Medelius ................ H01B 1/04 |
| | | 324/543 |
| 2012/0059248 A1 | 3/2012 | Holsing et al. |
| 2013/0257625 A1 * | 10/2013 | Holle ................... A61N 1/3752 |
| | | 340/687 |
| 2014/0187916 A1 * | 7/2014 | Clark .................. A61B 5/6885 |
| | | 600/424 |
| 2014/0275986 A1 | 9/2014 | Vertikov |
| 2015/0115742 A1 * | 4/2015 | Willis ................... H02H 1/003 |
| | | 307/125 |
| 2015/0316600 A1 * | 11/2015 | Davis .................. G01R 31/021 |
| | | 324/543 |
| 2016/0005193 A1 | 1/2016 | Markov et al. |

* cited by examiner

CABLE AND ASSOCIATED CONTINUITY MONITORING SYSTEM AND METHOD

SUMMARY

A cable, an associated continuity monitoring system and methods provide monitoring of the continuity of electric current of electrical components such as sensor signals from sensors used in connection with a medical apparatus.

In one embodiment, an example cable includes a proximal end configured to be electrically coupled with a processing unit of a medical apparatus, and a distal end configured to be electrically coupled to one or more sensors used with the medical apparatus. A sensor signal conductor for each sensor is configured to carry a signal from the sensor to the processing unit. An inductor coil is embedded in the distal end of the cable. An inductor coil conductor is configured to carry a continuity signal from the processing unit to the inductor coil.

During a medical procedure, for example, the continuity signal can be transmitted via the processing unit through the cable such that the continuity signal is imparted by the inductor coil to the sensor signal conductor with respect to each sensor. The imparted continuity signal is then carried back to the processing unit to indicate proper connectivity of the sensor signal with respect to each sensor.

The cable is preferably configured so that the inductor coil conductor is configured to conduct a continuity signal that is non-interfering with the sensor signals conducted by the sensor signal conductors. The distal end of the cable can be a connector for coupling with a sensor component connector configured for one or more sensors. Alternatively, the distal end of the cable can include one or more sensors, such as when the cable is configured as a cardiac catheter.

An example monitoring system includes a processing unit coupled to the proximal end of such a cable. The processing unit has a continuity signal generator having circuitry coupled to the proximal end of the cable's inductor coil conductor and a continuity signal detection unit coupled to the cable's sensor signal conductors configured with circuitry to detect the continuity signal returning on the sensor signal conductors. The continuity signal generator is preferably configured to generate a continuity signal that is non-interfering with sensor signals carried by the signal sensor conductors. The continuity signal unit circuitry can include filtering components to separate returning continuity signals from the sensor signals.

A display can be used to indicate the connectivity of the signal conductors of the cable based on detection of the continuity signal by the continuity signal detection unit. Accordingly, connection status information of sensors of a medical apparatus of which the monitoring system is a part can be displayed to a doctor or other operator of the medical apparatus.

An example method ensures proper communication of sensor signals during a medical procedure. A medical apparatus is provided that includes a processing unit and a cable that electrically couples one or more sensors to the processing unit via a sensor signal conductor with respect to each connected sensor. A continuity signal is transmitted via the processing unit through a continuity signal conductor of the cable such that the continuity signal is imparted to the sensor signal conductor at a distal end of the cable with respect to each connected sensor. The imparted continuity signal is carried back to the processing unit to indicate proper connectivity of the sensor signal with respect to each connected sensor. Preferably, the continuity signal is non-interfering with the sensor signals and is imparted to the sensor signal conductors by an inductor coil. Methodology may employ various embodiments of the cable such as those described above.

A continuity signal generator can generate the continuity signal and a continuity signal detection unit can detect the continuity signal returning on the sensor signal conductors. An associated display can be used to indicate the connectivity of the signal conductors of the cable based on detection of the continuity signal by the continuity signal detection unit. The method may further include separating returning continuity signals from sensor signals using a filtering circuitry.

Other examples include cables used with other electronic devices to electrically couple a processing unit of the device to one or more electrical components. An example cable includes a component conductor for each electrical component configured to carry an electrical current between the electrical component and the processing unit as well as an inductor coil embedded in the distal end of the cable. An inductor coil conductor is configured to carry a signal from the processing unit to the inductor coil. A continuity signal can be transmitted via the processing unit through the cable such that the continuity signal is imparted by the inductor coil to the component conductor with respect to each electrical component. The imparted continuity signal is then carried back to the processing unit to indicate proper connectivity of the electrical current with respect to each electrical component.

A monitoring system that includes such a cable coupled with the processing unit can have a continuity signal generator having circuitry coupled to a proximal end of the inductor coil conductor and a continuity signal detection unit coupled to the component conductors configured with circuitry to detect the continuity signal returning on the component conductors.

Other object and advantages of the invention will be apparent to those skilled in the art from the drawings and following detailed description.

BRIEF DESCRIPTION OF THE DRAWINGS

The present embodiments are illustrated by way of example, and not by way of limitation, in the figures of the accompanying drawings.

DETAILED DESCRIPTION OF THE EMBODIMENTS

Documents incorporated by reference in the present patent application may include terms that are defined in a manner that conflicts with the definitions made explicitly or implicitly in the present specification. In the event of any conflicts, the definitions in the present specification should be considered to be controlling.

During the conduct of medical procedures using modern medical equipment, a variety of sensors may be employs for various different functions that a physician relies upon for information.

Figure 1:
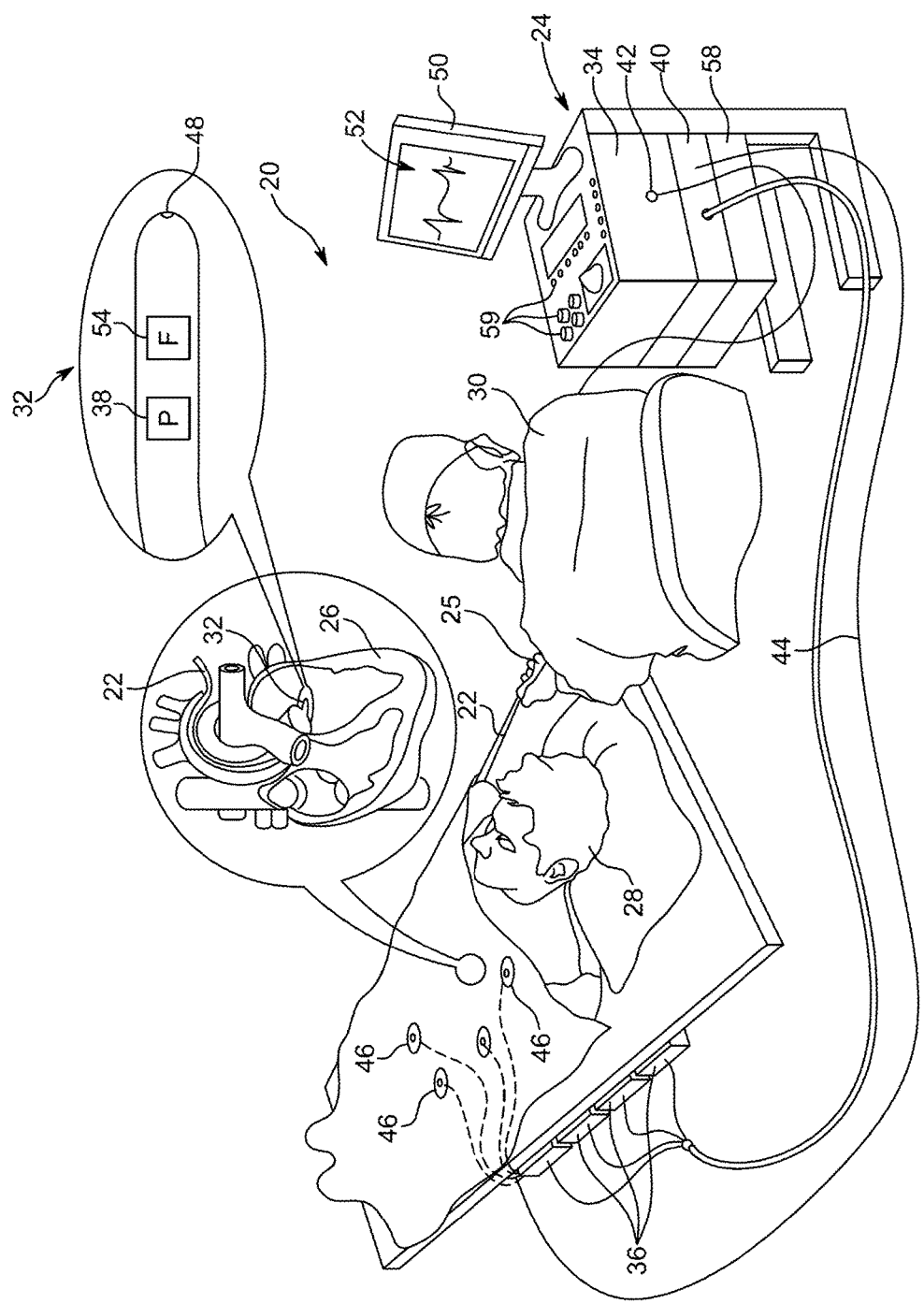
FIG. 1 is an example schematic, pictorial illustration of a medical system for conducting medical diagnostics and other procedures in accordance with the teachings of the present invention.
Figure 2A:
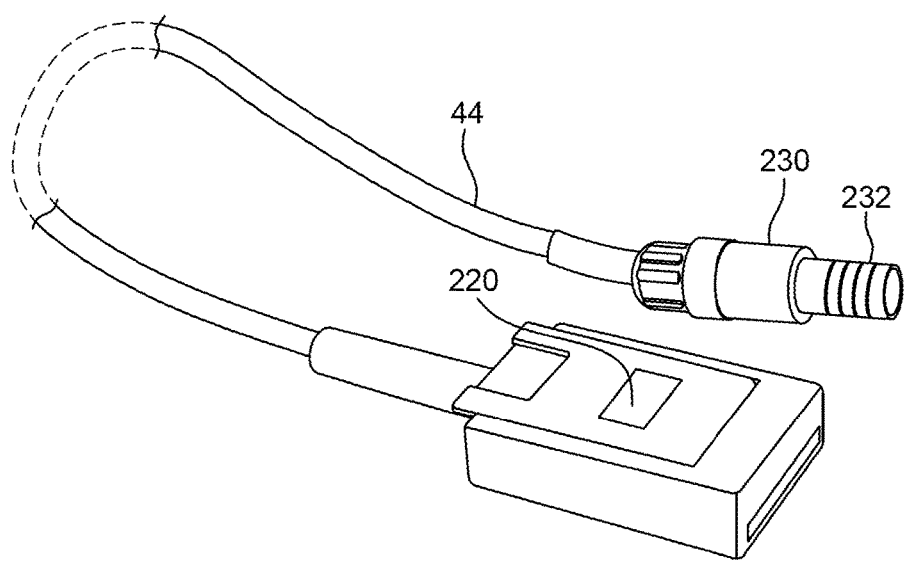
FIG. 2A is a perspective view of an example cable used in connection with the example medical system of FIG. 1 having distal and proximal connectors.
Figure 2B:
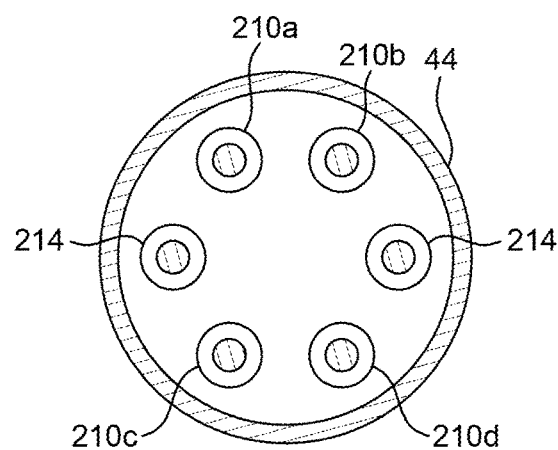
FIG. 2B is a cross section of a medial section of the cable of FIG. 2A.

For, example, FIG. 1 is an illustration of an example medical system 20 that is used to generate and display information 52 during a medical procedure and to control the deployment of various probes within a patient 28. The example system includes a probe 22, such as an intracardiac catheter, a console 24 and an associated probe control unit 25. The probe 22 can be used for diagnostic or therapeutic treatment, such as for example, mapping electrical potentials in a heart 26 of the patient 28 or performing an ablation procedure. Alternatively, the probe 22 can be used, mutatis mutandis, for other therapeutic and/or diagnostic purposes in the heart, lungs, or in other body organs and ear, nose, and throat (ENT) procedures.

A physician or other operator 30 can, for example, insert the probe 22 into the vascular system of the patient 28 using the probe control unit 25 so that a distal end 32 of the probe 22 enters a chamber of the patient's heart 26. The console 24 can use magnetic position sensing to determine position coordinates of the distal end 32 inside the heart 26. To determine the position coordinates, a driver circuit 34 in the console 24 may drive field generators 36 to generate magnetic fields within the body of the patient 28. The field generators 36 can include coils that may be placed below the torso of the patient 28 at known positions external to the patient 28. These coils may generate magnetic fields in a predefined working volume that contains the heart 26.

A position sensor 38 within the distal end 32 of the probe 22 can generate electrical signals in response to these magnetic fields. A signal processor 40 can process these signals in order to determine the position coordinates of the distal end 32 of the probe 22, including both location and orientation coordinates. Known methods of position sensing described hereinabove are implemented in the CARTO™ Navigation System produced by Biosense Webster Inc., of Diamond Bar, Calif., and is described in detail in the patents and the patent applications cited herein.

In this example, the position sensor 38 is configured to transmit a signal to the console 24 that is indicative of the location coordinates of the distal end 32. The position sensor 38 can, for example, comprise a type of magnetic sensor, or position transducers of other types, such as impedance-based or ultrasonic position sensors.

The probe 22 can also include a force sensor 54 contained within the distal end 32. The force sensor 54 can measure a force applied by the distal end 32 to the endocardial tissue of the heart 26 and generate a signal that is sent to the console 24. The force sensor 54 can include a magnetic field transmitter and a receiver connected by a spring in the distal end 32, and can generate an indication of the force based on measuring a deflection of the spring. Further details of this type of probe and force sensor are described in U.S. Patent Application Publications 2009/0093806 and 2009/0138007, and are incorporated herein by reference as if fully set forth. Alternatively, the distal end 32 can include another type of force sensor that can use, for example, fiber optics or impedance measurements.

The probe 22 can include an electrode 48 coupled to the distal end 32 and configured to function as an impedance-based position transducer. Additionally or alternatively, the electrode 48 can be configured to measure a certain physiological property, for example the local surface electrical potential of the cardiac tissue at one or more of the multiple locations. The electrode 48 can be configured to apply radio frequency (RF) energy to ablate endocardial tissue in the heart 26.

Although the example medical system 20 can be configured to measure the position of the distal end 32 using magnetic-based sensors, other position tracking techniques can be used (e.g., impedance-based sensors). Magnetic position tracking techniques are described, for example, in U.S. Pat. Nos. 5,391,199, 5,443,489, 6,788,967, 6,690,963, 5,558,091, 6,172,499, and 6,177,792, and are incorporated herein by reference as if fully set forth. Impedance-based position tracking techniques are described, for example, in U.S. Pat. Nos. 5,983,126 and 5,944,022, and are incorporated herein by reference as if fully set forth.

The signal processor 40 can be included in a general-purpose computer, with suitable front end and interface circuits for receiving signals from the probe 22 and controlling the other components of the console 24. The signal processor 40 can be programmed, using software, to carry out the functions that are described herein. The software can be downloaded to the console 24 in electronic form, over a network, for example, or it can be provided on non-transitory tangible media, such as optical, magnetic or electronic memory media. Alternatively, some or all of the functions of the signal processor 40 can be performed by dedicated or programmable digital hardware components.

In the example of FIG. 1, the console 24 is also connected by a cable 44 to external sensors 46. The external sensors 46 can include body surface electrodes and/or position sensors that can be attached to the patient's skin using, for example, adhesive patches. The body surface electrodes can detect electrical impulses generated by the polarization and depolarization of cardiac tissue. The position sensors can use advanced catheter location and/or magnetic position sensors to locate the probe 22 during use. Although not shown in FIG. 1, the external sensors 46 can be embedded in a vest that is configured to be worn by the patient 28. The external sensors 46 can aid in identifying and tracking the respiration cycle of the patient 28. The external sensors 46 are connected to transmit information to the console 24 via the cable 44.

During a diagnostic treatment, the signal processor 40 can present the information 52 and/or can store data representing the information 52 in a memory 58. The memory 58 can include any suitable volatile and/or non-volatile memory, such as random access memory or a hard disk drive.

The probe control unit 25 can be configured to be operated by the physician 30 to manipulate the probe based on the information 52 which is selectable using one or more input devices 59. Alternatively, the medical system 20 can include a second operator that manipulates the console 24 while the physician 30 operates the probe control unit 25 to manipulate the probe 22 based on the displayed information 52.

One option for treating cardiac arrhythmias can be an interventional catheter based procedure. An interventional catheter based procedure can involve a technique referred to as cardiac ablation. In such a procedure, a catheter is usually advanced from the groin area of a patient into the heart. Once in place, radio frequency (RF) energy can be delivered through the catheter to a specific location within a chamber of the subject's heart with the goal of re-establishing proper heart conduction.

Physicians utilizing complex medical systems such as the CARTO™ Navigation System are routinely in high pressure working environments where they are expected to rapidly master the operations of such equipment. Due to the inherent complexity of such tools and the variety of features therein, novel aspects of design geared towards increasing the usability and accessibility of these systems are welcome improvements. For example, in the event that the external sensor 46, the transduction electrode 48, the position sensor 38 or the force sensor 54 are generating unreliable or inconsistent signal during a procedure or otherwise, the physician or operator 30 would benefit from a reliable and intuitive feature indicating that these and other components are properly connected to the system 20.

Receiving reliable sensor data is an important factor in successfully performing such medical procedures. To permit use of medical equipment in hospitals, sensor cables may be required to meet various industry standards such as ANSI/AAMI EC53 promulgated by the American National Standards Institute (ANSI) and the Association for the Advancement of Medical Instrumentation (AAMI). Also, cables may be required to meet IEC 60601 which is a series of technical standards for the safety and effectiveness of medical electrical equipment, published by the International Electrotechnical Commission. Cables may also be beneficially manufactured to meet International DIN and CE Marking certifications.

Compliance with such standards can be looked upon as minimum requirements. In order to assure that reliable sensor information is being communicated to the console, the embodiments disclosed herein employ a monitoring system which utilizes an inductor coil to enable the generation of a signal indicating whether or not a given sensor or system component is properly connected.

FIGS. 2A-B and 3A-B illustrate an example configuration of the cable 44 used in connection with the example medical system of FIG. 1. In this example, the cable 44 contains sensor signal conductors 210a-d. The sensor signal conductors 210a-d are used to conduct signals from the sensors 46 to the processing unit 40 of the system console 24. A proximal connector 220 is used to electrically couple the cable 44 with the processing unit 40 of the console 24 via a mating console connector (not shown). A distal connector 230 is used to electrically couple the cable 44 with the sensors 46 via a mating sensor component connector (not shown).

Figure 3A:
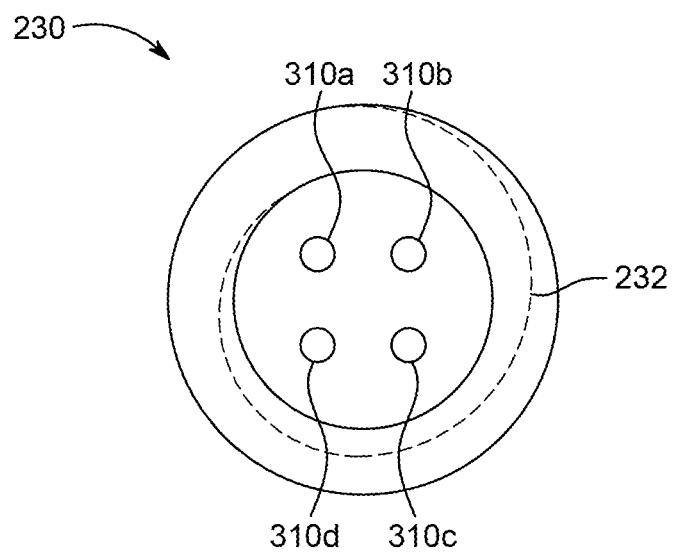
FIG. 3A is an end view of the distal connector of the cable of FIG. 2A.
Figure 3B:
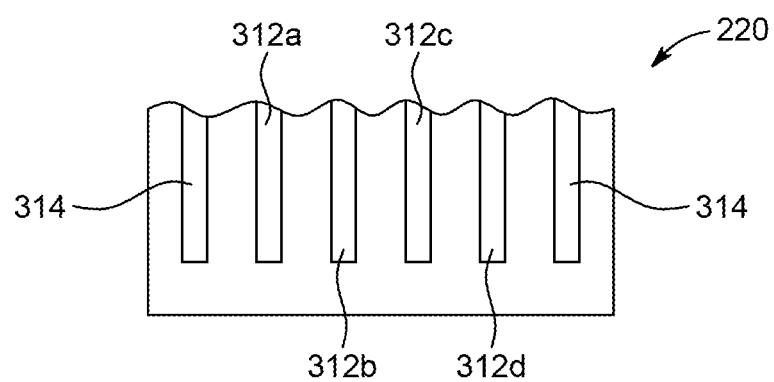
FIG. 3B is a cut-away end view of the proximal connector of the cable of FIG. 2A.

As best seen in FIG. 3A, the distal connector 230 includes contact pins 310a-d corresponding to the distal ends of respective sensor signal conductors 210a-d for mating with respective connector contact sockets of sensor signal wires of the sensors 46. As shown in FIG. 3B, the proximal connector 220 includes contacts 312a-d corresponding to proximal ends of respective sensor signal conductors 210a-d for mating with respective connector contacts of the console connector. Accordingly, the cable conducts respective sensor signals from the sensors 46 over the length of the cable 44 to the processing unit 40 when both ends are connected.

The distal connector 230 includes an embedded inductor coil 232 configured for connection to the processing unit 40 of the console 24 via two inductor coil conductors 214 and associated proximal connector contacts 314 of the cable 44. The processing unit is configured such that when the proximal connector 220 of the cable 44 is coupled to the console 24, a continuity circuit is formed so that a selected continuity signal can be sent from the processing unit 40 to the inductor coil 232. Upon receipt of the continuity signal sent from the processing unit 40, the embedded inductor coil 232 generates an electromagnetic field which imparts the continuity signal to each of the sensor signal conductors. Accordingly, when the cable 44 is coupled to both the sensors 46 and the console 24 while the continuity signal is generated, the signals conducted by the cable's sensor signal conductors 210a-d to the processing unit will each include both the sensor signal from the respective sensor 46 combined with the continuity signal provided the connections to the processing unit 40 are working properly. When the connections to the processing unit are not properly functioning, proper reception of the continuity signal will not occur.

The continuity signal is preferably generated based on a frequency or otherwise so as to be non-interfering with the signals generated by the sensors 46. This enables accurate reception of the sensor signals while also enabling relatively easy separation of the continuity signal from the sensor signals received at the console 24.

While the proximal connector 220 of the cable 44 in this example is specifically configured to couple directly with the console 24, the proximal connector 220 can be coupled with an extension cable (not shown) which is then connected to the console 24. In such an embodiment, the extension cable would include conductors corresponding to each of the cable sensor signal conductors as well as conductors for the continuity signal circuit. Proper return reception of the continuity signal in such a configuration will also indicate that the electrical couplings at both ends of the extension cable are also working properly.

Figure 4:
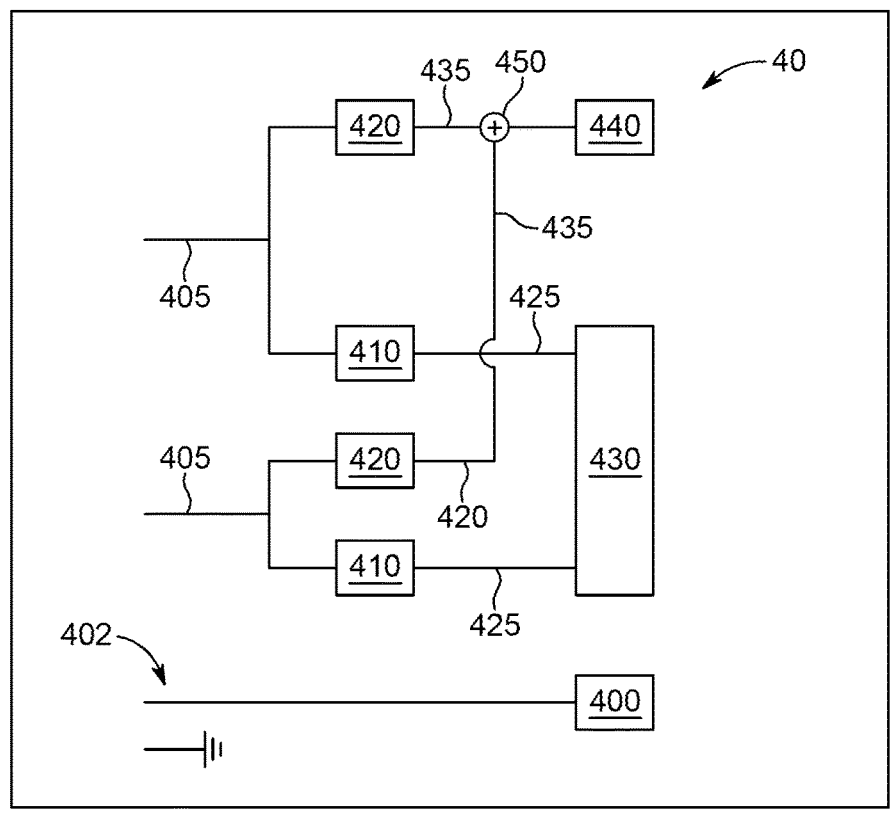
FIG. 4 is a schematic diagram of an example circuit configuration for use in processing continuity signals in accordance with the teachings of the present invention.

FIG. 4 provides an example circuitry configuration used in the processing unit 40 of console 24 to generate the continuity signal and process the separation of the combined sensor and continuity signals received from the cable 44. The processing unit 40 is configured with a signal circuit generator 400 with associated circuitry 402 that electrically couples with the inductor coil conductors 214 of the cable 44 to provide a selectively generated continuity signal to the inductor coil 232.

An input lead 405 (only two shown) can be provided to receive each respective combined sensor and continuity signal. Each combined signal is directed to first and second filters 410, 420. The first filters 410 are configured to filter the continuity signal from the sensor signal. The second filters 420 are configured to filter the sensor signal from the continuity signal. The post-filtering sensor signals 425 are then fed to a signal processor 430 to be processed in the usual manner for the type of sensor signal received.

The post-filtering continuity signals 435 are fed to a continuity signal detection unit 440. The post-filtering continuity signals can be individually fed to the continuity signal detection unit 440 for tracking the continuity of each individual sensor signal based on the presence or absence of the continuity signal. Alternatively, a combiner 450 can be provided to combine all of the post-filtering continuity signals 435 from a given cable to provide a signal of a sensor continuity failure of the cable when the combined post-filtering continuity signals 435 are less than a predetermined strength.

One example of generating the continuity signal to be non-interfering with the sensor signals is to generate a relatively high frequency continuity signal where the sensor signals are relatively low frequency. In such an example, the first filters 410 depicted in FIG. 4 can be configured as low-pass filters to filter out the high frequency continuity signal and the second filters 420 can be configured as high-pass filters to filter out the low frequency sensor signals.

Figure 5:
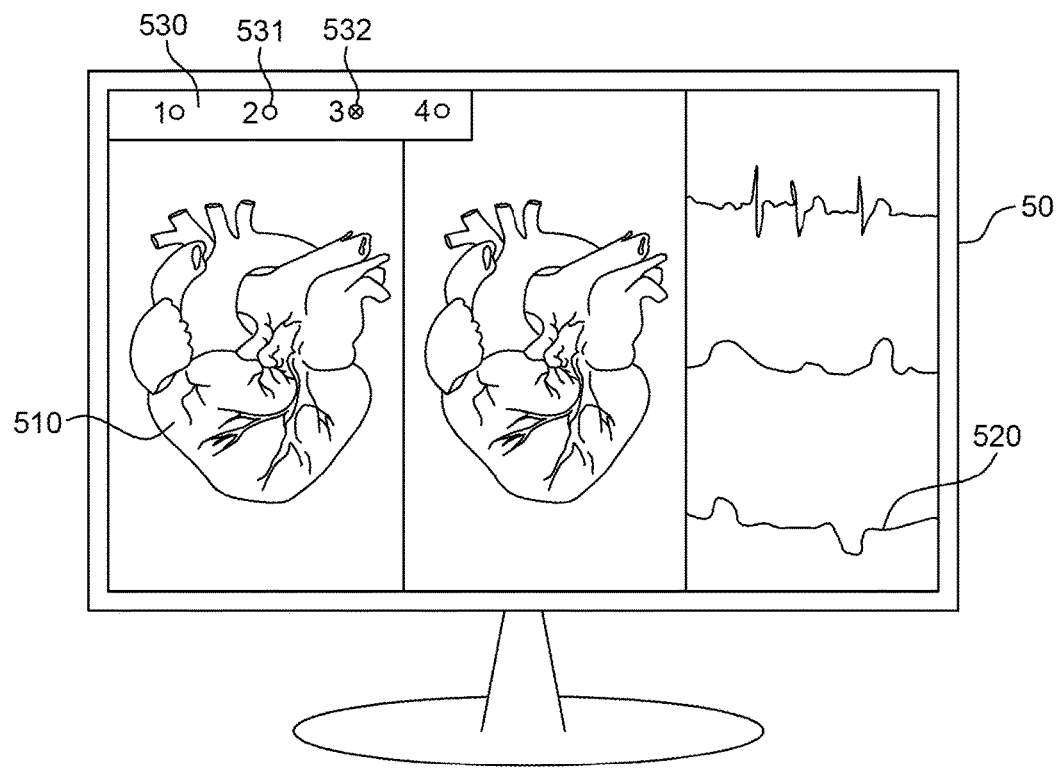
FIG. 5 is an elevated view of the monitor of the medical system of FIG. 1 displaying an example visual display in accordance with the teachings of the present invention.

FIG. 5 is an example of visual indications of proper connectivity of the sensor signals with respect to each sensor 64 as displayed on the display 50 during a cardiac procedure utilizing the medical system 20 of FIG. 1. In this example, cable 44 is used to connect the sensors 46 to the console 24 and individual post-filtering continuity signals 435 are fed to the continuity signal detection unit 440.

During such a procedure, one portion of the display may be used to display a three dimensional modeling of the heart 510 and electrocardiographic data 520 as supplied by the processing unit 40 and the various sensors. A sensor connection verification display 530 is provided to indicate connectivity of the four sensors 46 by respective sequentially numbered icons. Positive connection icons 531 are rendered as empty circles and negative connection icons 532, indicating a malfunctioning connection of a signal conductor, are rendered as a circle with an X. In this example, the sensory signal conductor corresponding to the third sensor did not convey properly to the continuity signal processing unit 440, and the operator 30 is thusly notified of the connection malfunction of the respective sensor 46 by the corresponding negative connection icon 532.

As will be appreciated by those skilled in the art, such warnings or alerts can be conveyed by audio, physical and/or other visual devices. The above described example display may be enhanced with additional notification mechanisms such as an auditory notification when a negative continuity signal is detected, or a flashing, enlarged, recolored, or otherwise distinguishable icon. Similarly, the complexity, size, placement, arrangement, iconography and other graphical elements of the sensor connection verification display 530 in this example are subject to variation according to user and designer preferences.

Figure 6:
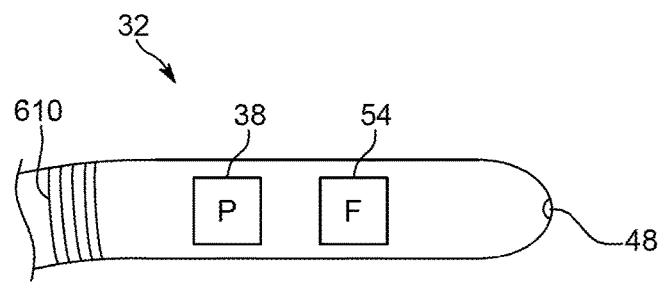
FIG. 6 is an enlarged view of the distal end of a probe made in accordance with the teachings of the present invention configured for use in the medical system of FIG. 1.

FIG. 6 illustrates a further embodiment where an inductor coil 610 is incorporated into the distal end 32 of the probe 22 used in conjunction with the medical apparatus 20 of FIG. 1. In this embodiment the coil 610 is associated with inductor coil conductors traversing the length of the probe such as conductors 214 of cable 44. Accordingly, the inductor coil 610 when connected in a continuity circuit as discussed above with respect to the inductor coil 231 of the cable 44, can be used to impart a continuity signal to sensor signal carrying conductors associated with the transduction electrode 48, the position sensor 38 and the force sensor 54 of the probe 22. As a result the continuity/connectivity of each of the probe's distal sensors 38, 54, 48 can be monitored on the display 50 in a manner similar to the sensors 46 as explained above with respect to FIG. 5 or otherwise as desired.

Although the above examples are directed towards monitoring the continuity of electrical currents in the form of sensor signals, the continuity of any type of electrical component current can be monitored using an analogous cable construction. For example, a cable can be provided for use in connection with a generic electrical apparatus where a proximal end is configured to be electrically coupled with a processing unit of the electrical apparatus and a distal end is configured with or to be electrically coupled to one or more electrical components used with the electrical apparatus that may or may not be sensors.

In such case, the cable may include a component conductor for each electrical component that is configured to carry an electrical current between the electoral component and the processing unit. The cable would also include an inductor coil embedded in the distal end of the cable and an inductor coil conductor configured to carry a signal from the processing unit to the inductor coil. A continuity signal can then be transmitted via the processing unit through the cable such that the continuity signal is imparted by the inductor coil to the component conductor with respect to each electrical component and carried back to the processing unit to indicate proper connectivity/continuity of the electrical current with respect to each said electrical component.

An example monitoring system can be constructed using such a cable coupled with the processing unit of the generic electrical apparatus. The example monitoring system could include a continuity signal generator having circuitry coupled to a proximal end of the inductor coil conductor, and a continuity signal detection unit coupled to the component conductors configured with circuitry to detect the continuity signal returning on the component conductors similar to those depicted in FIG. 4.

Other methodology and embodiments will be apparent to those skilled in the art and are within the scope of the invention.

What is claimed is:

1. A cable for use in connection with a medical apparatus comprising:
   a proximal end configured to be electrically coupled with a processing unit of the medical apparatus and a distal end configured with or to be electrically coupled to one or more sensors used with the medical apparatus;
   the cable including a sensor signal conductor for each sensor configured to carry a signal from the sensor to the processing unit; and
   the cable including an inductor coil embedded in the distal end of the cable and an inductor coil conductor configured to carry a signal from the processing unit to the inductor coil whereby during a medical procedure a continuity signal can be transmitted via the processing unit through the cable such that the continuity signal is imparted by the inductor coil to the sensor signal conductor with respect to each sensor and carried back to the processing unit to indicate proper connectivity of the sensor signal with respect to each sensor.

2. The cable according to claim 1 wherein the inductor coil conductor is configured to conduct a continuity signal that is non-interfering with the sensor signals conducted by the sensor signal conductors.

3. The cable according to claim 1 wherein the distal end of the cable is configured as a connector for coupling with a sensor component connector.

4. The cable according to claim 1 wherein the distal end of the cable is configured with at least one of the one or more sensors.

5. The cable according to claim 4 configured as a cardiac catheter.

6. A monitoring system comprising the cable according to claim 1 coupled with a processing unit; the processing unit including:
   a continuity signal generator having circuitry coupled to a proximal end of the inductor coil conductor; and
   a continuity signal detection unit coupled to the sensor signal conductors configured with circuitry to detect the continuity signal returning on the sensor signal conductors.

7. The monitoring system according to claim 6 further comprising a display configured to indicate the connectivity of the signal conductors of the cable based on detection of the continuity signal by the continuity signal detection unit.

8. The monitoring system according to claim 6 wherein the continuity signal generator is configured to generate a continuity signal that is non-interfering with sensor signals carried by the signal sensor conductors.

9. The monitoring system according to claim 8 wherein the continuity signal unit circuitry includes filtering components to separate returning continuity signals from the sensor signals.

10. A method for ensuring proper communication of sensor signals during a medical procedure:
providing a medical apparatus that includes a processing unit and a cable that electrically couples one or more sensors to the processing unit via a sensor signal conductor with respect to each connected sensor;
transmitting a continuity signal via the processing unit through a continuity signal conductor of the cable such that the continuity signal is imparted to the sensor signal conductor at a distal end of the cable with respect to each connected sensor and carried back to the processing unit to indicate proper connectivity of the sensor signal with respect to each connected sensor.

11. The method according to claim 10 wherein a continuity signal that is non-interfering with the sensor signals is the transmitted continuity signal and the continuity signal is imparted to the sensor signal conductors by an inductor coil.

12. The method according to claim 10 wherein the distal end of the cable is coupled to a sensor component connector.

13. The method according to claim 10 wherein the distal end of the cable is configured with at least one of the one or more sensors and the continuity signal is imparted to the sensor signal conductors by an inductor coil.

14. The method according to claim 13 wherein the cable is configured as a cardiac catheter used in the medical procedure.

15. The method according to claim 10 further comprising:
utilizing a continuity signal generator to generate a signal which is conducted between proximal and distal ends of the cable; and
utilizing a continuity signal detection unit to detect the continuity signal returning on the sensor signal conductors.

16. The method according to claim 15 further comprising utilizing a display to indicate the connectivity of the signal conductors of the cable based on detection of the continuity signal by the continuity signal detection unit.

17. The method according to claim 15 wherein the continuity signal generator generates the continuity signal as a continuity signal that is non-interfering with sensor signals carried by the signal sensor conductors.

18. The method according to claim 17 further comprising separating returning continuity signals from sensor signals using a filtering circuitry.

19. A cable for use in connection with an electrical apparatus comprising:
a proximal end configured to be electrically coupled with a processing unit of the electrical apparatus and a distal end configured with or to be electrically coupled to one or more electrical components used with the electrical apparatus;
the cable including a component conductor for each said electrical component configured to carry an electrical current between the electrical component and the processing unit; and
the cable including an inductor coil embedded in the distal end of the cable and an inductor coil conductor configured to carry a signal from the processing unit to the inductor coil whereby a continuity signal can be transmitted via the processing unit through the cable such that the continuity signal is imparted by the inductor coil to the component conductor with respect to each said electrical component and carried back to the processing unit to indicate proper connectivity of the electrical current with respect to each said electrical component.

20. A monitoring system comprising the cable according to claim 19 coupled with a processing unit; the processing unit including:
a continuity signal generator having circuitry coupled to a proximal end of the inductor coil conductor, and
a continuity signal detection unit coupled to the component conductors configured with circuitry to detect the continuity signal returning on the component conductors.

* * * * *